(12) United States Patent
Jacewicz et al.

(10) Patent No.: US 6,716,985 B2
(45) Date of Patent: Apr. 6, 2004

(54) PROCESS FOR MAKING PAROXETINE

(75) Inventors: Victor Withold Jacewicz, Tunbridge Wells (GB); Marvin Sungwhan Yu, Audubon, PA (US); Evgeny Shapiro, Haifa Bay (IL)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/138,553

(22) Filed: May 3, 2002

(65) Prior Publication Data

US 2002/0133011 A1 Sep. 19, 2002

Related U.S. Application Data

(63) Continuation of application No. 09/688,423, filed on Oct. 16, 2000, now abandoned, which is a continuation of application No. 09/087,632, filed on May 29, 1998, now Pat. No. 6,489,347.

(30) Foreign Application Priority Data

May 29, 1997 (GB) .............................. 9711095
Jul. 15, 1997 (GB) .............................. 9714875

(51) Int. Cl.[7] ..................... C07D 405/12; A61K 31/445
(52) U.S. Cl. ........................................ 546/197; 514/321
(58) Field of Search ..................... 514/321; 546/197

(56) References Cited

U.S. PATENT DOCUMENTS

| | | | |
|---|---|---|---|
| 2,498,432 A | 2/1950 | Lee ............... | 546/218 |
| 3,912,743 A | 10/1975 | Christensen ............. | 546/197 |
| 4,007,196 A | 2/1977 | Christensen et al. ........ | 546/197 |
| 4,585,777 A | 4/1986 | Christensen et al. ........ | 514/317 |
| 4,593,036 A | 6/1986 | Lassen et al. ............. | 514/317 |
| 4,861,893 A | 8/1989 | Borrett .................... | 546/185 |
| 4,902,801 A | 2/1990 | Faruk et al. .............. | 546/220 |
| 5,039,803 A | 8/1991 | Smith et al. .............. | 546/185 |
| 5,258,517 A | 11/1993 | Zepp et al. ............... | 546/240 |
| 5,328,917 A | 7/1994 | Jakobsen et al. ........... | 514/331 |
| 5,554,383 A | 9/1996 | Dodman ................... | 424/451 |
| 5,665,736 A | 9/1997 | Foguet et al. ............. | 514/321 |
| 5,681,962 A | 10/1997 | Callander ................. | 546/219 |
| 5,872,132 A | 2/1999 | Ward et al. ............... | 514/321 |
| 5,948,914 A | 9/1999 | Sugi et al. ................ | 546/240 |
| 6,051,712 A | 4/2000 | Binggeli ................. | 546/194 |

FOREIGN PATENT DOCUMENTS

| | | |
|---|---|---|
| EP | 0 190 496 | 8/1986 |
| EP | 0 300 617 | 1/1989 |
| EP | 0 374 674 | 6/1990 |
| EP | 0 802 185 | 10/1997 |
| EP | 0 812 827 | 12/1997 |
| ES | 2121685 | 12/1998 |
| WO | WO 96/36636 | 11/1996 |
| WO | WO 98/45263 | 10/1998 |
| WO | WO 00/26187 | * 5/2000 |

OTHER PUBLICATIONS

Miscovic et al., J. Chem. Soc., Perk Trans. 1, No. 16, pp. 2041–2050 (1996).

Carey, Organic Chemistry, McGraw–Hill Book Co., p. 566 (1987).

Chemical Abstracts 127:358789 (1997).

Chemical Abstracts 121:57525 (1992).

Chemical Abstracts 118:254964 (1992).

Chemical Abstracts 129:156928 (1996).

Koelsch, J. Am. Chem. Soc., vol. 65, pp. 2459–2460 (1943).

Peters et al., Chemical Abstract 132:321802.

* cited by examiner

*Primary Examiner*—Ceila Chang
(74) *Attorney, Agent, or Firm*—Wayne J. Dustman; Stephen Venetianer

(57) ABSTRACT

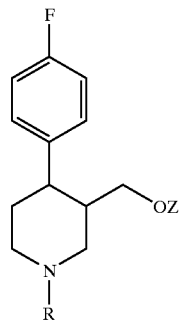

Compounds of structure (1) are obtained by reduction of compounds of the structures:

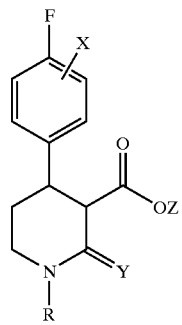

-continued
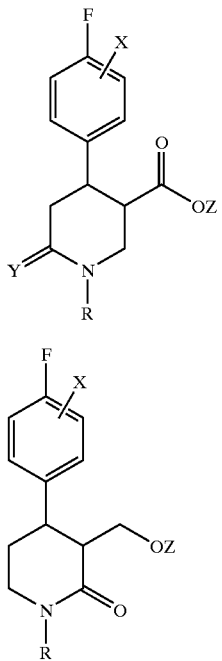
(2b)
(4a)
-continued
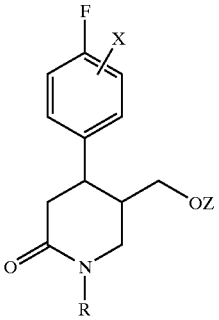
(4b)
Compounds of structure (1), especially where Z is a hydrogen atom or a 3,4-methylenedioxyphenyl group, are important intermediates for inter alia paroxetine.
1 Claim, No Drawings

PROCESS FOR MAKING PAROXETINE

This is a continuation of application Ser. No. 09/688,423 filed Oct. 16, 2000, now abandoned, which is a continuation of application Ser. No. 09/087,632, filed May 29, 1998, now U.S. Pat. No. 6,489,347.

The present invention relates to a new process for preparing pharmaceutically active compounds and intermediates therefor.

Pharmaceutical products with antidepressant and anti-Parkinson properties are described in U.S. Pat. No. 3,912,743 and U.S. Pat. No. 4,007,196. An especially important compound among those disclosed is paroxetine, the (−) trans isomer of 4-(4'-fluorophenyl)-3-(3',4'-methylenedioxy-phenoxymethyl)-piperidine. This compound is used in therapy as the hydrochloride salt to treat inter alia depression, obsessive compulsive disorder (OCD) and panic.

This invention aims to overcome disadvantages in the existing processes for preparation of such compounds and so to provide alternative processes for their manufacture.

This invention has been developed on the basis that compounds of structure (1) below are either valuable chemical intermediates useful for the manufacture of important medicinal products, for example paroxetine hydrochloride, or are themselves active compounds, such as disclosed in U.S. Pat. No. 3,912,743 and U.S. Pat. No. 4,007,196.

By reference to Example 4 of U.S. Pat. No. 4,007,196, paroxetine may be prepared from a compound of structure (1) below in which R is methyl, and Z is hydrogen, that is 4-(4'-fluorophenyl)-3-hydroxymethyl-1-methylpiperidine, by reaction with 3,4-methylenedioxyphenol followed by demethylation. In the same Example, 4-(4'-fluorophenyl)-3-hydroxymethyl-1-methyl piperidine is prepared by reduction of 4-(4'-fluorophenyl)-3-hydroxymethyl-1-methyl-1,2,3,6-tetra-hydropyridine (II), which is in turn prepared from 4-(4'-fluorophenyl)-1-methyl-1,2,3,6-tetrahydropyridine (III), by reaction with formaldehyde.

Alternative processes for the preparation of 4-(4'-fluorophenyl)-3-hydroxymethyl-1-methylpiperidine are given in EP-A-022334, by reduction of compounds of structure (A):

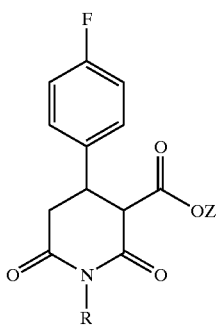

(A)

in which Z is alkyl and R is H, alkyl or aralkyl.

The above described processes produce compounds of structure (1) as a mixture of enantiomers. Therefore conversion of compounds of structure (1) to useful pharmaceuticals, such as paroxetine i.e. the (−) trans isomer of 4-(4'-fluorophenyl)-3-(3',4'-methylenedioxy-phenoxymethyl)-piperidine, will normally require a resolution stage, as described in EP-A-0223334.

This invention provides a process for the preparation of 4-aryl-piperidines of structure (1):

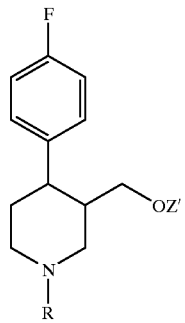

(1)

in which R is hydrogen or an alkyl, aralkyl, aryl, acyl, alkoxycarbonyl, arylalkoxycarbonyl, aryloxycarbonyl group, and Z' is a 3,4-methylenedioxyphenyl group, which comprises reduction of a compound of structure (2a) or (2b):

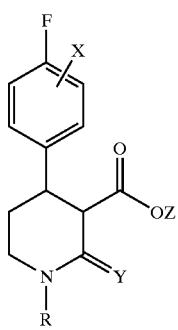

(2a)

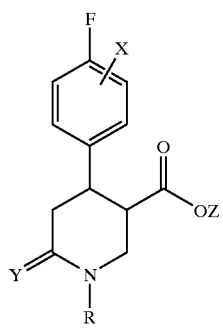

(2b)

in which

Y is oxygen or sulphur, and

R and X are as defined above and Z is hydrogen or an alkyl, aralkyl or aryl group, and where Z is other than a 3,4-methylenedioxyphenyl group thereafter converting Z to 3,4-methylenedioxyphenyl.

This invention also provides a process for the preparation of 4-aryl-piperidines of structure (1):

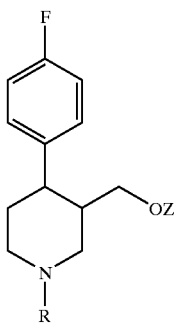
(1)

in which R is hydrogen or an alkyl, aralkyl, aryl, acyl, alkoxycarbonyl, arylalkoxycarbonyl, aryloxycarbonyl group, and Z is hydrogen or an alkyl, aralkyl or aryl group, most suitably where Z is a hydrogen atom or a 3,4-methylenedioxyphenyl group,
which comprises reduction of a compound of structure (2a) or (2b):

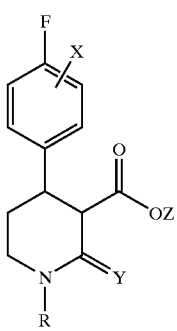
(2a)

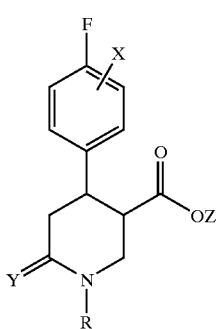
(2b)

in which
Y is oxygen or sulphur, and
R, X, and Z are as defined above.

When Z incorporates an aryl group, the aryl group, for example phenyl, may be optionally substituted by one or more groups such as halogen or alkyl or alkoxy, or by two substituents linked to form a fused ring. For example, an especially suitable substituent Z is 3,4-methylenedioxyphenyl, as found in paroxetine. Alkyl groups, including, alkyl groups that are part of other moieties such as alkoxy or acyl, are typically $C_{1-6}$, especially $C_{1-4}$ groups.

Compounds of structure (2a) and (2b) are believed to be novel and form part of this invention, especially compounds in which X is H, Z is H or 3,4-methylenedioxyphenyl and R is H or $C_{1-4}$alkyl, especially methyl.

In a first aspect of the process of this invention compounds of structure (2a) or (2b) are reduced to give compounds of structure (1) in which Z is H, that is 3-hydroxymethyl-4-aryl piperidines. Reduction may be accomplished by hydrogenation at atmospheric or above atmospheric pressure using a variety of known catalysts, or using hydride reagents such as lithium aluminium hydride and sodium borohydride, or by a combination of known methods. A particularly useful aspect of this invention is the transformation of 4-aryl-3-carboxyalkyl-1-(optionally substituted)-piperidines to 4-aryl-3-hydroxymethyl-1-(optionally substituted)-piperidines.

It will be appreciated that reduction of esters or carboxylic acids of structure (2) may be carried out stepwise and an intermediate may be isolated, for example a carboxaldehyde, and the reduction of these intermediate compounds to a compound of structure (1) is also included in the scope of this invention.

Intermediate carboxaldehydes are believed to be novel and form part of this invention. A particularly valuable intermediate is 4-(4-fluorophenyl)-5-oxopiperidine-3-carboxaldehyde.

In a second aspect of the process of this invention compounds of structure (2a) and (2b), where Z is not H, are reduced to ethers of structure (1). This may be accomplished by the use of known selective reagents such as diborane and DIBAL, or by Raney nickel desulphurization of a thionoester intermediate. A particularly advantageous ether for the manufacture of paroxetine is the 3,4-methylenedioxyphenyl ether.

Following the reduction to give an ether of structure (1), either or both the groups Z and R may be subsequently converted to a different group Z or R by conventional means, in order to produce the desired pharmaceutical agent. For example, in the preparation of paroxetine, it may be appropriate to convert Z=H to Z=3,4-methylenedioxyphenyl and/or R=$C_{1-4}$alkyl to R=H. This aspect is also included in the scope of this invention.

One advantageous aspect of this profess is that a single enantiomer of the intermediate (2) may be prepared either by enantioselective synthesis or from a chiral precursor, in which case the resolution noted above may be avoided entirely or transferred to an early stage in the overall process.

Starting materials of structure (2a), where Y is oxygen, may be prepared conveniently by carboxyalklyation of a 4-aryl-piperidine-2-one precursor, which may in turn be obtained from the reaction of an activated alkyl 3-aryl-5-hydroxyvalerate with an amine. In a particularly advantageous embodiment of this invention the alkyl 3-aryl-5-hydroxyvalerate is prepared as a single enantiomer by selective reduction of a 3-arylglutarate mono-ester obtained by enzymatic hydrolysis of the pro-chiral dialkyl 3-arylglutarate, for example using pig liver esterase to obtain S-enantiomers and -chymotripsin to obtain R-enantiomers. Suitable dialkyl 3-arylglutarates may be obtained by, for example, reaction of 4-fluorobenzaldehyde with methyl acetoacetate.

The ester group at the 3-position or a group convertible to an ester group may already be present in the starting material or may be introduced for example by reaction of a 2-piperidone of structure (3) firstly with a strong base, such as sodium hydride or lithium hexamethyldisilazide followed by a carboxylating agent, such as a chloroformic ester or thiono chloroformic ester.

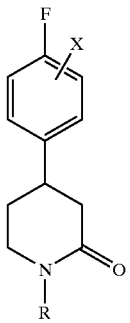

(3)

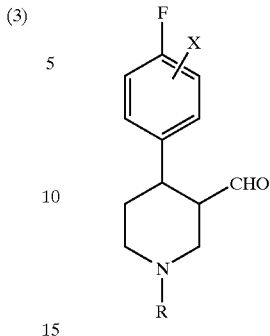

(2d)

Compounds with structure (2b) where Y is oxygen may be prepared by, for example, reductive cyclisation of 2-cyano-3-(4'-fluorophenyl)-glutarate esters. A similar preparation has been described for the preparation of 3-ethoxycarbonyl-4-(3'-methoxyphenyl)-2-piperidone (Journal of Organic Chemistry (1977) volume 42, pages 1485–1495), but this procedure had been found to be unsuitable for the preparation of compounds with structure (2b) and results in a complex misture of products. A new and efficient process has now been discovered in which 2-cyano-3-(4'-fluorophenyl)glutarate esters, especially diethyl 2-cyano-3-(4'-fluorophenyl)glutarate, are hydrogenated in 1,4-dioxane. Such compounds may be prepared by reaction of, for example, ethyl cyanoacetate and ethyl 4-fluorocinnamate in sodium ethoxide.

Compounds of structure (2a) and (2b) where Y is sulphur can be prepared from the cyclization of analogous thionoesters or by the reaction of piperidones with sulphurizing reagents such as Lawesson's reagent or phosphorus pentasulphide, as described in Organic Syntheses (1984), volume 62, page 158 and the Journal of Organic Chemistry (1981) volume 46, page 3558. Reduction of the thiopiperidones may be accomplished stepwise, particularly if a reagent such as Raney nickel is used for the first stage. The resulting 4-aryl-3-carboxyalkylpiperidines may then be separately reduced to compounds of structure (1) by conventional reduction, most suitably with hydride reagents such as lithium aluminium hydride.

Suitable starting materials of structure (2) can be prepared by the manner described above or by transesterification of intermediate esters.

It will be appreciated that the reduction of compounds of structure (2) to give compounds of structure (1) may take place stepwise via. inter alia, compounds of structure (2c) and (2d):

and the reduction of these intermediate compounds, when produced by this process is also included in the scope of this invention.

Compounds of structure (2c) where X is hydrogen, Z is methyl, and R is hydrogen or $C_{1-4}$alkyl, were described in U.S. Pat. No. 4,007,196, though no procedure was described which is satisfactory for large scale manufacture. These problems have been overcome in the pending application GB9700690.2. The preparation of compounds of structure (2c), where R and Z are alkyl, by reduction of quaternary pyridinium salts have also been described in EP 0219934.

Compounds of structure (2c) other than those described in the above mentioned patent applications and compounds of structure (2d) are novel and form part of this invention. Particularly important compounds of structure (2c) are those where Z is aryl, especially 3,4-methylenedioxyphenyl, which may inter alia be prepared by selective reduction of compounds (2a) or (2b) or by transesterification of other compounds (2c). Compounds of structure (2c) and (2d) may be reduced further to compounds of structure (1).

Alternatively, interrupted or selective reduction of compounds (2a) and (2b) may give rise to novel intermediate alcohols or ethers of structure (4a) or (4b) which may be isolated, and which also form part of this invention:

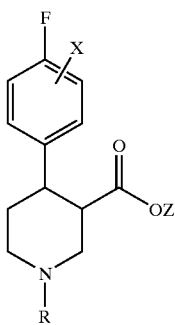

(2c)

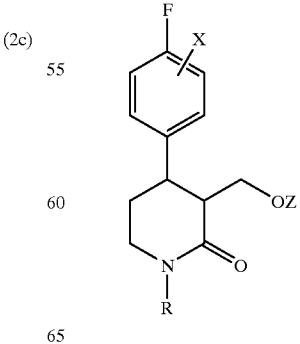

(4a)

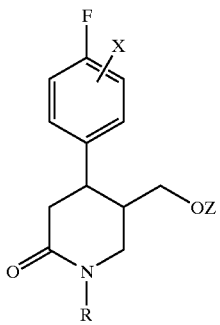
(4b)

In a preferred method for the preparation of compounds of structure (4a) and (4b), compounds of structure (2a) an (2b) are first converted into thioesters which are desulphurised with, for example, Raney nickel. The intermediate thiono esters are also novel and form part of this invention.

Compounds of structure (4a) and (4b) may also be separately prepared by reactions analogous to those described above for the preparation of compounds of structure (2a) and (2b) and employed in the processes of this invention. For example a carbinol of structure (4a) may be prepared by hydroxymethylation of compound (3), and an ether group may be introduced by reaction of (3) with a chloromethyl ether.

Particularly important compounds of structure (4a) and (4b) are those where Z is 3,4-methylenedioxyphenyl, and especially where X and R are both hydrogen. Compounds of structure (4) may be reduced further to compounds of structure (1).

The novel compounds of structure (4) may also be prepared by other methods such as etherification of (4) where Z is hydrogen, or reductive alkylation of aldehydes.

Many of the intermediate compounds in the processes of this invention are novel, and such intermediates form another aspect of this invention.

In a further aspect of the invention, a compound of structure (1) in which Z is a hydrogen atom obtained by processes of this invention may be converted to an active compound disclosed in U.S. Pat. No. 3,912,743 and U.S. Pat. No. 4,007,196 using conventional procedures disclosed therein.

In particular the compound of structure (1) in which in which Z is a hydrogen atom may be used to prepare paroxetine. The paroxetine is preferably obtained as the hydrochloride salt and most preferably as the hemihydrate of that salt, as described in EP-A-0223403. The present invention includes within its scope the compound paroxetine, particularly paroxetine hydrochloride, especially as the hemihydrate, when obtained via any aspect of this invention, and any novel intermediates resulting from the described procedures.

Paroxetine obtained using this invention may be formulated for therapy in the dosage forms described in EP-A-0223403 or WO96/24595, either as solid formulations or as solutions for oral or parenteral use.

Therapeutic uses of paroxetine, especially paroxetine hydrochloride, obtained using this invention include treatment of: alcoholism, anxiety, depression, obsessive compulsive disorder, panic disorder, chronic pain, obesity, senile dementia, migraine, bulimia, anorexia, social phobia, premenstrual syndrome (PMS), adolescent depression, trichotillomania, dysthymia, and substance abuse, referred to below as "the Disorders".

Accordingly, the present invention also provides:
a pharmaceutical composition for treatment or prophylaxis of the Disorders comprising paroxetine or paroxetine hydrochloride obtained using the process of this invention and a pharmaceutically acceptable carrier,
the use of paroxetine or paroxetine hydrochloride obtained using the process of this invention to manufacture a medicament in solid or liquid form for the treatment or prophylaxis of the Disorders; and
a method of treating the disorders which comprises administering an effective or prophylactic amount of paroxetine or paroxetine hydrochloride obtained using the process of this invention to a person suffering from one or more of the Disorders.

This invention is illustrated by the following Examples.

EXAMPLE 1

Dimethyl 3-(4'-fluorophenyl)glutarate

4-Fluorobenzaldehyde (75 ml), methyl acetoacetate (150 ml), piperidine (10 ml), and methanol (235 ml), were stirred for 8 hours at ambient temperature. The precipitate was filtered, washed twice with cold methanol (2×75 ml), resuspended in methanol (150 ml), treated with a mixture of a 25% solution of sodium methoxide in methanol (650 ml) and water (54 ml), and heated at reflux for 7 hours. After cooling, solvent (500 ml) was removed by vacuum distillation, water (1 litre) was added, and a further quantity of solvent removed by distillation (100 ml). The mixture was extracted with tert-butyl methyl ether (400 ml), acidified to pH less than 3 with concentrated hydrochloric acid, and extracted with tert-butyl methyl ether (3×300 ml). The extracts were evaporated and the tert-butyl methyl ether replaced by methanol (800 ml). Concentrated hydrochloric acid (10 ml) was added, the mixture heated at reflux for 12 hours, and the solvent partially removed by evaporation. Dilution with water (75 ml) gave crystals of dimethyl 3-(4'-fluorophenyl)glutarate. Yield after drying 124.1 g (71%).

EXAMPLE 2

S-3-(4'-fluorophenyl)glutaric acid monomethyl ester

A solution of dimethylformamide in water (20%, 7 litres) was adjusted to pH 7.0 with 1.0 M phosphate buffer, and dimethyl 3-(4'-fluorophenyl)glutarate (160 g) added. The mixture was held at 37° C., pig liver esterase (46 ml, 96,000 U) added, and the reaction continued for 24 hours at constant temperature and pH. The mixture was cooled, acidified to below pH 3 with hydrochloric acid, and extracted with tert-butyl methyl ether (3×1500 ml). The extracts were washed with dilute hydrochloric acid (2×1 litre), reduced to about 1 litre by evaporation, treated with hexane (100 ml), and cooled to 0° C. to crystallize the product. The supernatant liquors were decanted, evaporated to 200 ml, and treated with hexane (50 ml) to give further crystals. The yield of crystalline (S-enantiomer) mono-ester after drying was 118.8 g (78%).

The R-enantiomer is obtained by an analogous procedure using -chymotrypsin (Can. J. Chem., 1994. 72(11), 2312).

EXAMPLE 3

R-1-benzyl-3-(4'-fluorophenyl)-piperidine-2-one

A solution of S-3-(4'-fluorophenyl)glutaric acid monomethyl ester in tetrahydrofuran (800 ml) was treated with lithium hydride (2.65 g) and heated at reflux for 1 hour. After cooling, a lithium borohydride solution (108 ml, 2 molar) was added slowly and the mixture heated at reflux for 12 hours, then cooled to ambient temperature. Dimethylformamide (400 ml) and methyl sulphate (56.6 ml) were added and the mixture heated at reflux for 5 hours, cooled, quenched with methanol (80 ml), and after 30 minutes diluted with toluene (1500 ml) and washed with 10% ammonium chloride solution (3×800 ml). The toluene phase was evaporated to about 400 ml, diluted with toluene (1 litre) and evaporated again to 400 ml; this was repeated twice more.

Toluene (600 ml) and triethylamine (96 ml) were added to the crude methyl 3-(4'-fluorophenyl)-5-hydroxyvalerate, the mixture cooled to 0° C. then slowly treated with methanesulphonyl chloride (32 ml). The mixture was stirred for 45 minutes at 0° C. filtered through silica, and the cake washed with toluene (100 ml). Triethylamine (100 ml), benzylamine (40 ml), and sodium iodide (2 g) were added to the filtrate and the mixture heated at reflux for 20 hours, then cooled and washed with 2 molar hydrochloric acid (3×600 ml) and saturated sodium hydrogen carbonate (2×500 ml). The resulting solution of crude R-1-benzyl-3-(4'-fluorophenyl)-piperid-2-one was evaporated to about 300 ml and diluted with heptane (50 ml) to induce crystallization.

Yield of dried product 52.6 g (56%, >99% ee).

EXAMPLE 4

S-1-benzyl-3-(4'-fluorophenyl)-piperidine-2-one

S-1-benzyl-3-(4'-fluorophenyl)-piperidine-2-one is prepared from S-3-(4'-fluorophenyl)glutaric acid monomethyl ester by an analogous prosedure in which the initial reduction is carried out with borane. Similarly R-1-benzyl-3-(4'-fluorophenyl)-piperidine-2-one may be prepared from R-3-(4'-fluorophenyl)glutaric acid monomethyl ester.

EXAMPLE 5

Trans-(4R)-1-benzyl-3-carboxymethyl-4-(4'-fluorophenyl)-piperidine-2-one

A solution of R-1-benzyl-4-(4'-fluorophenyl)-piperidine-2-one (2.0 g) in toluene (40 ml) was treated with sodium hydride (0.704 g, 60% dispersion in oil) and dimethyl carbonate (3.0 ml), and heated at reflux for 14 hours. After cooling the reaction mixture was quenched with ice, treated with methanol (15 ml), and potassium carbonate (0.5 g) and stirred for 1 hour. Toluene (100 ml) was added and the phases were separated. The organic phase was washed with 1 molar hydrochloric acid (2×50 ml), saturated sodium hydrogen carbonate solution (2×50 ml), and water (50 ml). The organic phase was evaporated and the crude trans-(4R)-1-benzyl-3-carboxymethyl-4-(4'-fluorophenyl)-piperidine-2-one crystallised from tert-butyl methyl ether and hexane. Yield 1.56 g (65%).

Example 6

Preparation of trans-(4R)-1-benzyl-4-(4'-fluorophenyl)-3-hydroxymethyl piperidine A solution of trans (4R)-1-benzyl-3-carboxymethyl-4-(4'-fluorophenyl)-piperidine-2-one (1.97 g) in tetrahydrofuran (20 ml) was treated with borane-tetrahydrofuran complex (19.6 ml, 1 molar) and heated at reflux for 6 hours. After cooling, the reaction was quenched with 1 molar hydrochloric acid, then stirred and heated at reflux for a further 1 hour. The mixture was cooled to ambient temperature, the pH adjusted to 9 with 1 molar sodium hydroxide, and extracted with ethyl acetate (3×20 ml). The combined organic extracts were washed with saturated sodium chloride and evaporated to give trans-(4R)-1-benzyl-4-(4'-fluorophenyl)-3-hydroxymethylpiperidine (1.59 g, 92%).

EXAMPLE 7

Preparation of Paroxetine Hydrochloride a) trans-(4R)-1-benzyl-4-(4'-fluorophenyl)-3-hydroxymethylpiperidine (9.65 g), p-toluenesulphonyl chloride (6.18 g), dimethylaminopyridine (0.1 g), and triethylamine (5.0 ml) in toluene (150 ml) were stirred for 42 hours at ambient temperature. The mixture was diluted with toluene (100 ml), washed with saturated sodium hydrogen carbonate (3×150 ml) and water (100 ml). The organic layer was evaporated to minimum volume, and diluted with toluene (100 ml). A solution of sesamol (4.28 g) in dimethyl formamide (150 ml) was reacted with sodium hydride (1.26 g), added to the activated carbinol solution, and the mixture heated at 60° C. for 16 hours. The mixture was cooled, diluted with toluene (200 ml), washed with 1 molar sodium hydroxide (2×100 ml) and water (2×100 ml), and evaporated to an oil. Yield 9.83 g (79%).

b) The oil from Example 7(a) (4.0 g) was dissolved in isopropanol (40 ml) and acetic acid (4 ml) and hydrogenated with 5% palladium on charcoal catalyst (2.0 g,) at 70 psi and 50° C. for 2 hours. The cooled mixture was filtered through celite, the celite washed with isopropanol (40 ml) and the filtrate diluted with toluene (100 ml). The solution was washed with saturated sodium hydrogen carbonate (2×100 ml), 1 molar sodium hydroxide (100 ml), then water (100 ml), and finally with saturated sodium chloride (100 ml). The organic phase was evaporated to low volume (15 ml), treated with concentrated hydrochloric acid (2 ml) and isopropanol (15 ml). The crystalline paroxetine hydrochloride was isolated, washed and dried. Yield 2.1 g.

EXAMPLE 8

Diethyl 2-cyano-3-(4-fluorophenyl)-glutarate

A mixture of ethyl cyanoacetate (13.56 g) and ethyl 4-fluorocinnamate (19.4 g) was added to a solution of sodium ethoxide (2.3 g sodium in 50 ml ethanol) at 60° C. over 2–3 minutes and the mixture heated under reflux for 1 hour then cooled to 5° C. Glacial acetic acid (6 ml) was added slowly to the reaction mixture at below 5° C. The bulk of the ethanol was removed by distillation at reduced pressure the residue diluted with water (40 ml), extracted with toluene (3×30 ml), and the combined organic phases dried over anhydrous magnesium sulphate. The solution was filtered, evaporated to an oil (28.6 g), and distilled at 166–180° C. at 3.5 mbar to produce diethyl 2-cyano-3-(4-fluorophenyl)-glutarate (23 g, 74% yield, 98% purity).

EXAMPLE 9

3-Carboxyethyl-4-(4'-fluorophenyl)-piperidine-6-one

Diethyl 2-cyano-3-(4-fluorophenyl)-glutarate (15.3 g), platinum oxide (0.57 g), and hydrogen chloride gas in dioxane (0.1 mole in 50 ml) were hydrogenated at 185 psi and 60° C. for 6.5 hours. The product was cooled, filtered, and evaporated, and the residue was dissolved in chloroform (130 ml) and washed with saturated sodium bicarbonate (200 ml). The solution was dried and passed through activated carbon (Darco G-40) to remove colloidal platinum and evaporated to give crude 3-carboxyethyl-4-(4'-fluorophenyl)-piperidine-6-one. This product was repeatedly treated in ethyl acetate solution with activated carbon to give a purified product as mixture of isomers (9.3 g, 70%, 95.6% purity).

EXAMPLE 10

3-Carboxyethyl-4-(4'-fluorophenyl)-piperidine-6-one

Diethyl 2-cyano-3-(4-fluorophenyl)-glutarate (85.0 g, 0.22 mol), platinum oxide (2.1 g), and 4 molar hydrogen chloride gas in dioxane (112 ml, 0.45 mol) were stirred in a Parr apparatus under hydrogen (90–195 psi) at 60° C. for 18 hours. The residue was filtered and evaporated and then dissolved in chloroform (300 ml), washed with saturated sodium bicarbonate solution (250 ml), dried, filtered through activated carbon (Darco G-40) to remove colloidal platinum, and evaporated to give the title compound (72.1 g, 84%) as an oil which crystallised on standing. Recrystallisation from hexane-dichloromethane gave a product with a cis/trans ratio 88:12, m.p. 139–141° C.

EXAMPLE 11

4-(4-Fluorophenyl)-3-hydroxymethylpiperidine

Borane-tetrahydrofuran complex (1.0 molar solution in tetrahydrofuran (10.8 ml, 10.8 mmol) was added over 20 hours in 3 stages (in 3.6 mmol portions) at a rate of 7 ml/hour by means of a syringe pump to a solution of 4-(4-fluorophenyl)-3-carboxyethylpiperidin-6-one (0.53 g, 2 mmol, trans/cis~1:1) in tetrahydrofuran (3 ml) at 26° C. The reaction mixture was stirred for 1 hour after addition of the last portion of the borane solution. then quenched with 3.5 ml 30% aqueous potassium carbonate solution. The phases were separated and the aqueous phase extracted with diethyl ether (25 ml). The organic phases were combined and evaporated to yield 0.43 g of the title compound. Yield 80%.

EXAMPLE 12

4-(4-Fluorophenyl)-3-hydroxymethylpiperidine

Lithium aluminum hydride (1.0 molar solution in tetrahydrofuran, 0.75 ml, 0.75 mmol) was added gradually to a solution of trans-4-(4-fluorophenyl)-3-carboxyethylpiperidin-6-one (0.25g, 0.836 mmol) in tetrahydrofuran (3 ml) keeping the temperature below 25° C. The reaction mixture was stirred for 1 hour at 25° C., then quenched with 1 drop of water, followed by 2 drops 15% sodium hydroxide solution, and finally with 5 drops of water. Extraction with dichloromethane (35 ml) followed by evaporation of the dichloromethane phase gave 0.21 g of the title compound. Yield 76%.

EXAMPLE 13

4-(4-Fluorophenyl)-3-carboxyethylpiperidine 4-(4-fluorophenyl)-3-carboxyethylpiperidin-6-one (12.0 g, 0.045 mol, trans/cis-ratio~1:1) was added in one portion to a solution of trimethyloxonium fluoroborate (12.0 g, 0.081 mol) in dichloromethane (80 ml) and the resulting solution stirred, at 14–18° C., for 60 hours under an argon atmosphere. The solvent was removed in vacuo, and then the residue was dissolved in absolute ethanol (100 ml), heated to 45° C. and treated with sodium borohydride (10.0 g, 0.26 mol) in 1.0 g portions, allowing the mixture to boil under reflux. Most of the solvent was evaporated and the residue quenched with water (60 ml) followed by concentrated hydrochloric acid. After neutralization with 10% sodium bicarbonate solution the products were extracted with dichloromethane (150 and 50 ml). The extracts were dried with anhydrous sodium sulphate, filtered, and evaporated to afford the title compound as a cis/trans mixture (1:1). Yield 75%. A portion of the product was purified by column chromatography (silica gel, eluted with ethyl acetate-triethylamine, 98:2).

Under the same conditions, trans-4-(4-fluorophenyl)-3-carboxyethylpiperidine was prepared from trans-enriched 4-(4-fluorophenyl)-3-carboxyethylpiperidin-6-one.

EXAMPLE 14

3-Carboxy-4-(4-fluorophenyl)piperidine-6-one

A solution of 4-(4-fluorophenyl)-3-carboxyethylpiperidin-6-one (2.0 g, 0.0075 mol) in ethanol (10 ml) was added to a solution of sodium hydroxide (0.4 g, 0.01 mol) in 95% ethanol and the mixture brought to reflux and stirred for 2.5 hours. The solvent was then removed by evaporation at reduced pressure, and the residue neutralized with 10% aqueous hydrochloric acid (25 ml) and extracted with ethyl acetate (3×20 ml). After separation, the combined organic phases were dried with anhydrous sodium sulphate, filtered. and evaporated to give only 0.1 g of a white solid. The aqueous phase was therefore lyophilized and the residue extracted with hot methanol. The residue, consisting of inorganic salts, was discarded while the methanol extracts were combined and evaporated at reduced pressure to give the title compound (1.34 g, 75%).

EXAMPLE 15

4-(4-Fluorophenyl)-3-[(3,4-methylenedioxyphenyl)oxycarbonyl]-piperidine-6-one A solution of 4-(4-fluorophenyl)-3-carboxyethylpiperidin-6-one (0.5 g, 1.88 mmol, trans/cis ratio 56:44) in ethanol (10 ml) was added to a solution of sodium hydroxide (0.08 g, 2 mmol) in 95% ethanol (5 ml) and the mixture heated for 4 hours at 60° C. The solvent was removed at reduced pressure and the residue of water removed by distillation with toluene. The residue was suspended in dichloromethane (5 ml), treated with a solution of thionyl chloride (0.24 g, 2 mmol), and the mixture was brought to reflux. After 1 hour evolution of sulphur dioxide ceased, so the mixture was cooled to room temperature and treated with pyridine (0.16 g, 2 mmol) followed by a solution of sesamol (0.24 g, 1.75 mmol) in chloroform (2.5 ml). The resulting mixture was brought to reflux, heated for 4 hours, and stirred at ambient temperature for 2 days. The solvent was then removed at reduced pressure and the residue treated with water (5 ml), then extracted with ethyl acetate (20 and 10 ml). The organic extracts were combined, washed with brine (20 ml), dried over anhydrous sodium sulphate, filtered and evaporated to give the title compound (0.32 g).

EXAMPLE 16

4-(4-Fluorophenyl)-3-formylpiperidine-6-one

DIBAL-H (4.03 ml, 6 mmol) was added gradually at a rate of 5.6 ml/hour, by means of a syringe pump, to a solution of 3-carboxyethyl-4-(4-fluorophenyl)-piperidine-6-one (0.53 g, 2 mmol) in 4 ml tetrahydrofuran at −70° C. under an argon atmosphere. The reaction mixture was stirred for 1 hour at −70° C. then quenched with a solution of methanol (0.24 ml) in toluene (2 ml) at −70° C., followed by 0.12 ml water at 0° C. After 30 minutes stirring at ambient temperature, the gel which formed was destroyed by the addition of 1.5 ml brine and the reaction mixture was extracted with diethyl ether (50 ml). The organic phase was separated, dried with anhydrous sodium sulphate, filtered and evaporated to yield the title compound (0.2 g) as a yellow oil. The aqueous layer was basified with 10% aqueous sodium hydroxide and extracted with dichloromethane (20 ml). A further 0.08 g product was isolated from the dichloromethane extract.

EXAMPLE 17

4-(4-Fluorophenyl)-3-hydroxymethylpiperidine-6-one

DIBAL-H (15.1 ml, 0.0225 mol) was added at a rate of 50 ml/hour, by means of a syringe pump, to a solution of 3-carboxyethyl-4-(4-fluorophenyl)-piperidine-6-one (1.99 g, 0.0075 mol) in tetrahydrofuran (15 ml) at −70° C. under an argon atmosphere keeping the temperature below 0° C. The mixture was allowed to warm to 23° C. and stirred for 45 minutes, then a solution of methanol (0.9 ml) in toluene (7.5 ml) was added to destroy the excess DIBAL-H, followed by 30% potassium carbonate solution (8.5 ml), all below 30° C. The organic phase was separated, dried with anhydrous sodium sulphate, filtered, and evaporated to afford the title compound (1.54 g) as a slightly colored oil, which was crystallized by trituration with ether. Yield 67%.

Recrystallization from ether-ethyl acetate gave a product with >96% purity, m.p. 188.8–191.6° C.

EXAMPLE 18

4-(4-Fluorophenyl)-3-[(3,4-methylenedioxyphenyl) oxymethyl]-piperidine-6-one

To a solution of 4-(4-fluorophenyl)-3-hydroxymethylpiperidine-6-one (0.36 g, trans/cis ratio>95:5) and dimethylethylamine (0.25 g) in dichloromethane (6 ml) was added a solution of benzenesulphonyl chloride (0.34 g, 0.25 ml, 1.94 mmol) in dichloromethane (4 ml). The mixture was homogenised with N,N-dimethylformamide (1 ml) and stirred at ambient temperature for 5 hours during which time more dimethylethylamine was added in aliquots (2.5 ml over 2.5 hours making a total of 0.5 ml). The mixture was then quenched with water (15 ml), the phases separated, and the aqueous phase extracted with dichloromethane (20 ml). The combined organic phases were washed with brine (10 ml) and evaporated to give 0.56 g of the O-benzenesulphonate intermediate. This product was dissolved in N,N-dimethylformamide (6 ml), mixed with a solution of sesamol (0.25 g, 1.81 mmol) in N,N-dimethylformamide (4 ml), and treated with 1 drop of water. Sodium methoxide (0.28 g, 5.14 mmol) was added slowly to the solution, keeping the temperature at approximately 20° C., then the temperature was raised to 50° C. and maintained for 6.5 hours. The mixture was then quenched with water (30 ml), the phases separated, and the aqueous phase extracted with diethylether (3×50 ml). The combined organic extracts were washed with a 15% sodium hydroxide solution (2×35 ml) and brine (50 ml), dried with anhydrous sodium sulphate, filtered, and evaporated to give crude 4-(4-fluorophenyl)-3-[(3,4-methylenedioxyphenyl)oxymethyl]-piperidine-6-one (0.24 g). This product was purified by column chromatography (silica gel eluted with ethyl acetate/methanol gradient with 2% triethylamine).

EXAMPLE 19

4-(4-Fluorophenyl)-3-[(3,4-methylenedioxyphenyl) oxymethyl]piperidine

A solution of lithium aluminium hydride in tetrahydrofuran (1.0M solution, 2 ml, 2.0 mmol) was added over ten minutes to a well stirred solution of 4-(4-fluorophenyl)-3-[(3,4-methylenedioxyphenyl)oxymethyl]piperidine-6-one (0.41 g, 0.96 mmol) in tetrahydrofuran (7 ml), maintaining the temperature below 25° C. The reaction solution was stirred for 2 hours and then quenched first of all with water (0.16 ml), then with 15% aqueous sodium hydroxide solution (0.1 ml), and finally with water again (0.4 ml). The reaction mixture was stirred for 0.5 hours to complete the precipitation, diluted with dichloromethane (30 ml) and filtered. The filtrate was evaporated in vacuo to give the title product with a trans/cis ratio=72:28. Yield 90%.

Column chromatography on silica gel 60 (elution with a mixture of ethyl acetate:methanol:triethylamine=80:20:5) yielded a pure product as the transisomer.

What is claimed is:

1. A process for the preparation of 4-aryl-piperidines of structure (1):

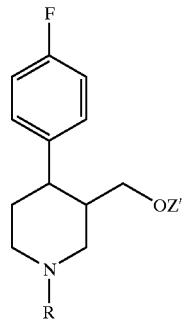

(1)

in which R is hydrogen or an alkyl, aralkyl, aryl, acyl, alkoxycarbonyl, arylalkoxycarbonyl, aryloxycarbonyl group; and Z' is a 3,4-methylenedioxyphenyl group;

which process comprises converting a compound of structure (4c) or (4d):

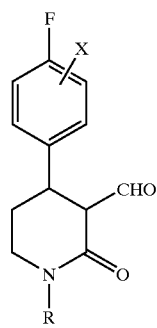

(4c)

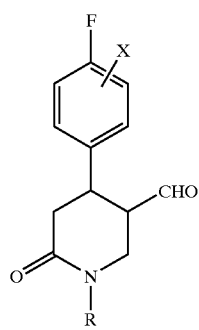

(4d)

in which
R is hydrogen or an alkyl, aralkyl, aryl, acyl, alkoxycarbonyl, arylalkoxycarbonyl, aryloxycarbonyl group; and
X is hydrogen or from one to four reducible groups;
into a compound of structure (1).

* * * * *